US00PP25962P2

(12) United States Plant Patent
Harrison

(10) Patent No.: US PP25,962 P2
(45) Date of Patent: Sep. 29, 2015

(54) ***LOMANDRA* PLANT NAMED 'ROMA 13'**

(50) Latin Name: *Lomandra longifolia*
Varietal Denomination: Roma 13

(71) Applicant: Robert Harrison, Tynong (AU)

(72) Inventor: Robert Harrison, Tynong (AU)

( * ) Notice: Subject to any disclaimer, the term of this patent is extended or adjusted under 35 U.S.C. 154(b) by 195 days.

(21) Appl. No.: 13/987,884

(22) Filed: Sep. 12, 2013

(51) Int. Cl.
*A01H 5/12* (2006.01)

(52) U.S. Cl.
USPC ..... Plt./373

(58) Field of Classification Search
USPC ..... Plt./373, 263.1, 384
CPC ..... A01H 5/12
See application file for complete search history.

*Primary Examiner* — Kent L Bell

(57) ABSTRACT

A new cultivar of *Lomandra* plant named 'Roma 13' that is characterized by a compact habit, arching narrow flat variegated leaves that are grey-green with a white center stripe and white margins.

1 Drawing Sheet

Botanical classification: *Lomandra longifolia*.
Variety denomination: 'Roma 13'.

BACKGROUND OF THE INVENTION

The present invention relates to a new and distinct cultivar of *Lomandra* plant botanically known as *Lomandra longifolia* and hereinafter referred to by the cultivar name 'Roma 13'.

'Roma 13' originated from seed collected from an open pollinated bed of unnamed *Lomandra longifolia* cultivars. The resulting seeds were subsequently planted and grown. The exact parent plants are unknown. The cultivar 'Roma 13' was selected by the inventor in 2008 as a single plant within the progeny in Tynong, Victoria, Australia.

Asexual reproduction of the new cultivar 'Roma 13' first occurred by division in 2008 in Tynong, Victoria, Australia. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Lomandra* cultivar 'Roma 13'. These traits in combination distinguish 'Roma 13' as a new and distinct cultivar apart from other existing known varieties of *Lomandra*.

1. *Lomandra* 'Roma 13' exhibits arching narrow flat leaves.
2. *Lomandra* 'Roma 13' exhibits leaves that are grey-green with a white center stripe and white margins.
3. *Lomandra* 'Roma 13' exhibits a compact habit.

The closest comparison cultivars are *Lomandra* 'LM400' (U.S. Plant Pat. No. 15,583) and *Lomandra* 'LM300' (U.S. Plant Pat. No. 15,420).

'Roma 13' is distinguishable from 'LM400' by the following characteristics:

1. 'Roma 13' has leaves that are grey-green with a white center stripe and white margins. In comparison, the leaves of 'LM400' are solid blue-grey in color.

'Roma 13' is distinguishable from 'LM300' by the following characteristics:

1. 'Roma 13' has leaves that are grey-green with a white center stripe and white margins. In comparison to 'LM300', the leaves of 'LM300' are solid yellow-green in color.

BRIEF DESCRIPTION OF THE DRAWING

The accompanying photograph illustrates the distinguishing traits of *Lomandra* 'Roma 13'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Lomandra* cultivar named 'Roma 13'. Data was collected in Auckland, New Zealand from 18 month old outdoor grown plants in 20 cm. diameter containers. The time of year was Fall in the Southern Hemisphere and the average temperature was 24 degrees Centigrade during the day and 11 degrees Centigrade at night. Color determinations are in accordance with The Royal Horticultural Society Colour Chart 2007 edition, except where general color terms of ordinary dictionary significance are used. The growing requirements are similar to the species. 'Roma 13' has not been tested under all possible conditions and phenotypic differences may be observed with variations in environmental, climatic, and cultural conditions, however, without any variance in genotype.

Botanical classification: *Lomandra* 'Roma 13'.
Annual or perennial: Perennial.
Parentage: The exact parent plants of 'Roma 13' are unknown.
Vigor: Strong.
Growth habit: Upright, arching.
Plant shape: Tufting grass.
Suitable container size: 14 cm. and larger pots.
Height: 70 cm. in height.

Width: 105 cm. in width.
Low temperature tolerance: −8° Centigrade.
High temperature tolerance: 45° Centigrade.
Propagation: Division.
Time to produce a rooted cutting or liner in summer: 80 days at 21° Centigrade.
Time to produce a rooted cutting or liner in winter: 120 days at 15° Centigrade.
Crop time: 12 months.
Root system: Fine and fibrous.
Rhizomes:
*Rhizome dimensions.*—4 cm. in length and 0.5 cm. in diameter.
*Rhizome texture*.—Smooth.
*Rhizome color.*—155C.
Foliage:
*Leaf arrangement*.—Tussock.
*Compound or single*.—Single.
*Leaf shape*.—Linear.
*Leaf apex*.—Praemorse.
*Leaf base*.—Sheathed.
*Leaf length.*—65 cm. in length.
*Leaf width.*—4.5 mm. in width.
*Texture*.—Glabrous both sides.
*Pubescence*.—Absent.
*Leaf margin*.—Entire.
*Venation pattern*.—Linear.
*Young leaf color* (*upper surface*).—191A, center stripe 158A and margins 158A.
*Young leaf color* (*lower surface*).—191A, center stripe 158A and margins 158A.
*Mature leaf color* (*upper surface*).—191A, center stripe 158A and margins 158A.
*Mature leaf color* (*lower surface*).—191A, center stripe 158A and margins 158A.
*Vein color*.—Same as leaf (both surfaces).
Flower: Flower initiation and development has not been observed on plants of the new *Lomandra* to date.
Disease and pest resistance: Disease and pest resistance has not been observed.

The invention claimed is:

1. A new and distinct variety of *Lomandra* plant named 'Roma 13' as described and illustrated.

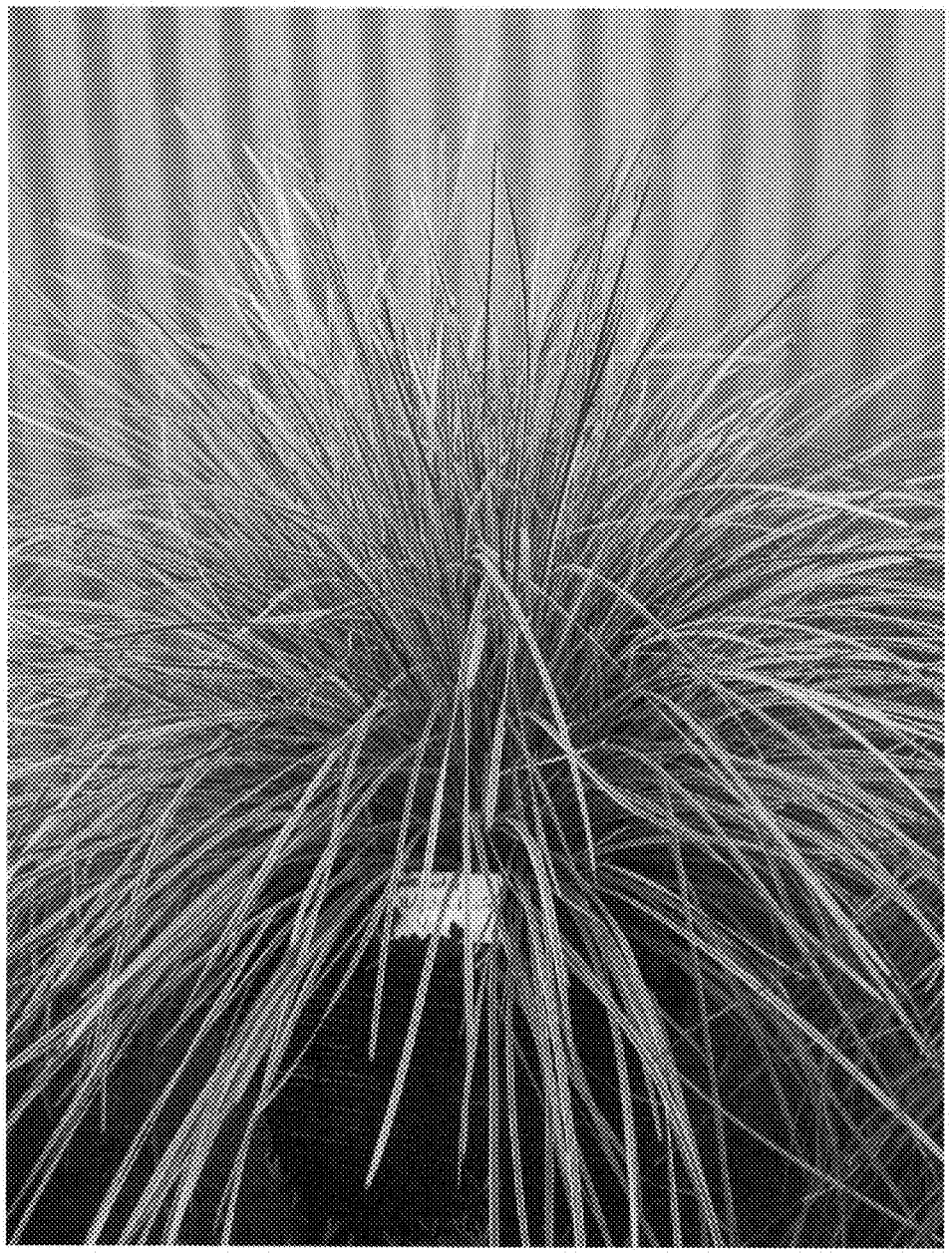

* * * * *